United States Patent
Brown

(10) Patent No.: US 9,655,785 B2
(45) Date of Patent: May 23, 2017

(54) ARCH STRAP FOR TREATING HEEL PAIN

(75) Inventor: Adam C. Brown, Hollywood, SC (US)

(73) Assignee: Adam C. Brown, Charleston, SC (US)

( * ) Notice: Subject to any disclaimer, the term of this patent is extended or adjusted under 35 U.S.C. 154(b) by 710 days.

(21) Appl. No.: 12/852,940

(22) Filed: Aug. 9, 2010

(65) Prior Publication Data

US 2012/0035522 A1   Feb. 9, 2012

(51) Int. Cl.
*A61F 13/06* (2006.01)

(52) U.S. Cl.
CPC .................. *A61F 13/064* (2013.01)

(58) Field of Classification Search
CPC .. A61F 5/00; A61F 5/01; A61F 5/0111; A61F 5/0113; A61F 5/04; A61F 5/042; A61F 5/14; A61F 5/32; A61F 13/00; A61F 13/02; A61F 13/0273; A61F 13/06; A61F 13/065; A61F 13/566; A61F 5/0127; A61F 5/0585; A61F 13/066; A61F 5/0102; A61F 13/067; A43B 7/20
USPC ........ 602/65, 66, 20, 21, 22, 61, 23, 27, 28; 66/178, 185; 36/8.3, 102, 145, 114, 140, 36/11.5, 4, 8.1, 88, 89, 91, 50.1, 103, 36/115, 7.3, 51, 58.5, 58.6; 2/239
See application file for complete search history.

(56) References Cited

U.S. PATENT DOCUMENTS

| | | | | |
|---|---|---|---|---|
| 1,788,852 A | * | 1/1931 | Arthur | 602/66 |
| 2,591,378 A | * | 4/1952 | Scholl | 602/30 |
| 2,708,930 A | * | 5/1955 | Lowman | 602/27 |
| 3,198,192 A | * | 8/1965 | O'Brien | 602/10 |
| 5,453,083 A | * | 9/1995 | Kasahara | 602/30 |
| 5,554,107 A | | 9/1996 | Shannahan | |
| 5,620,413 A | | 4/1997 | Olson | |
| 5,755,679 A | * | 5/1998 | Selner et al. | 602/27 |
| 5,865,779 A | | 2/1999 | Gleason | |
| 6,120,473 A | * | 9/2000 | Oliverio | 602/66 |
| 6,142,967 A | * | 11/2000 | Couch | 602/66 |
| 6,228,045 B1 | * | 5/2001 | Gaylord et al. | 602/27 |
| 6,379,321 B2 | * | 4/2002 | Gaylord et al. | 602/27 |
| 6,558,339 B1 | | 5/2003 | Graham | |
| 6,573,419 B2 | * | 6/2003 | Naimer | 602/41 |
| 6,602,216 B1 | | 8/2003 | Nordt, III | |
| 7,056,299 B2 | | 6/2006 | Brown et al. | |
| 7,329,792 B2 | * | 2/2008 | Buckman et al. | 602/53 |
| 2005/0228332 A1 | * | 10/2005 | Bushby | 602/61 |
| 2006/0161090 A1 | * | 7/2006 | Lee | 602/66 |
| 2008/0269655 A1 | * | 10/2008 | Shoukry | 602/28 |

* cited by examiner

*Primary Examiner* — Ophelia A Hawthorne

(57) ABSTRACT

An arch strap for the treatment of pain in a patient's heel, such as plantar fasciitis, posterior tibial tendonitis and capsulitis. The arch strap has a first portion serving as a pad, shaped and sized to fit under the arch beneath a patient's foot and extending upwardly along one side of the patient's foot to the medial portion of the foot. The first portion is preferably adhesively attached to the arch of the foot and provides support and stability to the foot when properly positioned. There is an elongated strip having a first end attached to one side of the first portion and extending around the patient's heel and positioned in the medial portion of the foot where it adhesively attaches to the foot. The elongated strip keeps the first portion in place and provides support in the patient's heel to relieve pain.

4 Claims, 1 Drawing Sheet

ARCH STRAP FOR TREATING HEEL PAIN

BACKGROUND OF THE INVENTION

1. Field of the Invention

The present invention relates to a method for treating heel pain. More particularly, this invention relates to an arch strap for the treatment of foot pain.

2. Description of Related Art

One of the most common foot complaints is heel pain. Heel pain is an uncomfortable and often debilitating condition caused by a variety of reasons generally associated with physical activity which entails repeated impact and strain of the tissues on the bottom of the foot. Such problems may include plantar fasciitis, posterior tibial tendonitis and capsulitis of the foot.

The plantar fascia is the connective tissue on the bottom of the foot which is attached at the front to the metatarsal phalangeal joints, i.e., the metatarsal or toe joints, and to the rear at the calcaneus or heel bone. The plantar fascia acts like a stabilizing structure for the forces developed during physical activities. During walking and running activities the plantar fascia stretches and contracts, and is subject to impact and strain. Continuous stress of the plantar fascia can cause loss of the natural elasticity or supporting function of the tissue. This resulting loss of elasticity can produce physical symptoms that include tenderness, swelling, and pain.

To relieve the pain and promote healing usually requires removal of the cause of the condition. Among the treatments are rest to limit activities that are likely to aggravate the injury; ice to help reduce the pain and swelling in the area; and/or stretching of the calf muscle group helps to relieve the tension on the foot in walking and at rest by allowing the foot to function properly. Other treatments may include anti-inflammatory medication to reduce the pain and inflammation associated with the injury and to speed recovery; strapping the foot to rest the injured site without limiting activity and to temporarily correct mechanical abnormality in foot function; orthotics to correct mechanical deformity in the bony structure of the foot; and cortisone injections when other treatments are found to be ineffective. In severe cases surgery may be required.

Despite prior efforts to develop a method for effectively and inexpensively treating heel pain, there remains a desire for an easy to use method to treat plantar fasciitis, posterior tibial tendonitis and capsulitis of the foot, and to provide a simple, easy to use means for doing so.

SUMMARY OF THE INVENTION

It is therefore the general object of the present invention to provide a method for relieving heel pain due to plantar fasciitis, posterior tibial tendonitis and capsulitis of the foot.

Another object of the present invention is to provide an arch strap for alleviating and/or reducing pain in a patient's foot.

Yet another object of the present invention is to provide an arch strap to fit under the arch of a patient's foot and extending upwardly along one side of the patient's foot to the medial portion of the foot and having an elongated strip extending around the patient's heel to the other side of the patient's foot to provide support to the arch portion of the strap.

The arch strap of the present invention is especially suitable for the treatment of plantar fasciitis, posterior tibial tendonitis and capsulitis of the foot. The heel pain strap comprises a first portion serving as a pad, shaped and sized to fit under the arch beneath a patient's foot along the lateral portion of the foot from the fifth metatarsal head to the back of the heel and extending upwardly along one side of the patient's foot to the medial portion of the foot. The first portion is preferably adhesively attached to the arch of the foot and provides support and stability to the foot when properly positioned on a patient. The first portion is preferably made from a material such as Elastoplast®. In a preferred embodiment the arch pad of the first portion is generally rectangular being about 3.5 to 5.0 inches wide, depending upon the width of the patient's foot.

There is an elongated strip having a first end attached to one side of the first portion and extending around the patient's heel and positioned in the medial portion of the foot where it adhesively attaches to the foot. The elongated strip is typically about 8 to 12 inches long from the rear end of the first portion. The elongated strip is preferably an adhesive elastic tape such as Elastoplast® elastic adhesive bandage. The elongated strip serves to keep the first portion in place and to provide tension in the patient's heel to relieve pain.

There is also provided a method for alleviating and/or reducing pain in a patient's heel which comprises securing a first portion shaped and sized to fit under the arch beneath a patient's foot along the lateral portion of the foot from the fifth metatarsal head to the back of the heel and extending upwardly along one side of the patient's foot to the medial portion of the foot and applying tension to an elongated strip having a first end attached to one side of the first portion and extending around the patient's heel to a second end positioned at the other side of the foot.

Other objects, features and advantages of the present invention will become apparent from the following detailed description of the invention taken in conjunction with the accompanying drawings.

BRIEF DESCRIPTION OF THE DRAWINGS

Having described the invention in general terms, reference will now be made to the accompanying drawings, which are not necessarily drawn to scale, and wherein.

DESCRIPTION OF THE PREFERRED EMBODIMENT(S)

The present invention now will be described more fully hereinafter with reference to the accompanying drawings, in which preferred embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art. Like numbers refer to the elements throughout.

Figure 1:
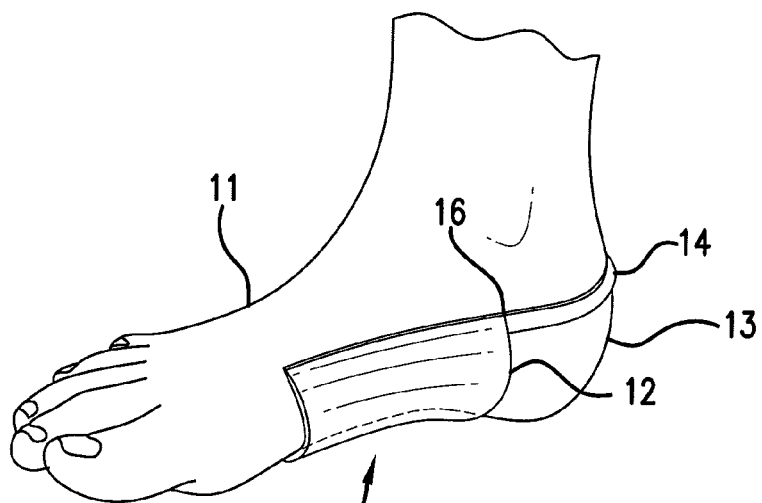
FIG. 1 is an isometric view showing an embodiment of the arch strap of the present invention positioned on a patient's foot showing the arch pad.

The present invention relates to an arch strap for alleviating heel pain associated with such problems such as plantar fasciitis, posterior tibial tendonitis and capsulitis of the foot. Referring now to FIG. 1 there is shown a preferred embodiment of the arch strap of the present invention. The arch strap 10 comprises a first portion 12, serving as an arch pad, shaped and sized to fit under the arch beneath a patient's foot 11 along the lateral portion of the foot from the fifth metatarsal head to the back of the heel and extending upwardly along one side of the patient's foot 11 to the medial portion of the foot. The first portion 12 is preferably adhesively attached to the arch of the foot. This first portion 12 of the arch strap 10 provides support and stability to the foot when properly positioned on a patient. The thickness of the first portion 12 should be thick enough to provide support under the arch but not so thick as to adversely effect the patient's walking. The first portion 12 is preferably made from a supportive material such as an elastic adhesive tape. The cushioning material has an adhesive backing that is covered by a non-stick protective layer that is removed when the arch strap 10 is put into place on the patient's foot. In a preferred embodiment, such as shown in FIG. 3, the arch pad of the first portion 12 is generally rectangular being about 3.5 to 5.0 inches wide depending upon the width of the patient's foot.

Figure 2:
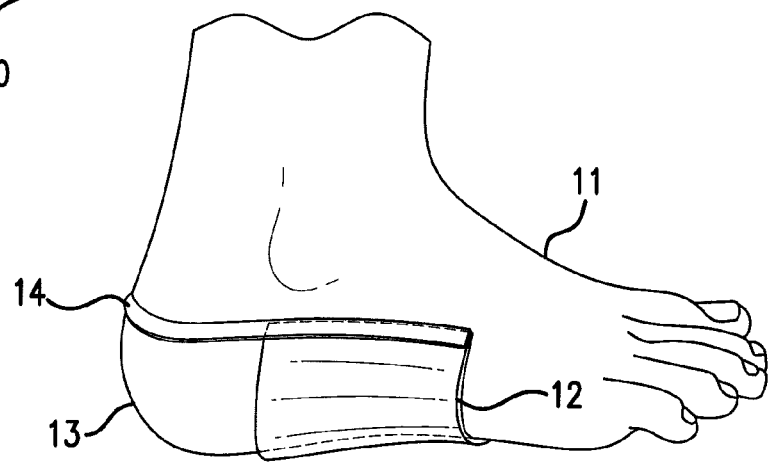
FIG. 2 is a perspective view of the embodiment shown in FIG. 1 showing the heel of the foot during use showing the elongated strip in position around the heel of a patient.

There is an elongated strip 14 having a first end attached to one side 16 of said first portion 12 and extending around the patient's heel 13 and positioned in the medial portion of the foot where it adhesively attaches to the foot 18, as more clearly shown in FIG. 2. The elongated strip 14 is typically about 8 to 12 inches long from the rear end of the first portion 12. The elongated strip 14 is preferably an adhesive elastic tape such as Elastoplast® elastic adhesive bandage. The elongated strip 14 serves to keep the first portion in place and to provide support in the patient's heel to relieve pain.

Figure 3:
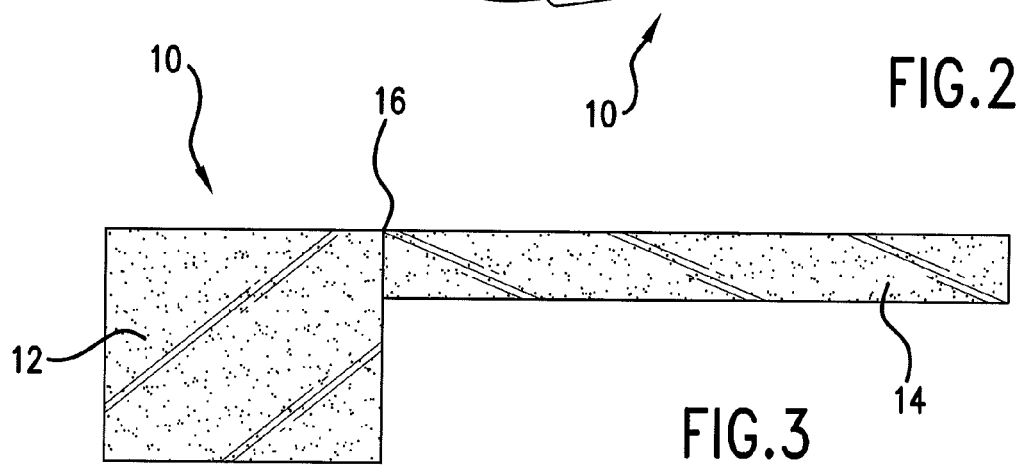
FIG. 3 illustrates a top plan view of the arch strap of the present invention.

As shown in FIG. 3, the adhesive backing of the first portion 12 is covered by non-stick strips that can be removed in the following order: the adhesive tape will then be pulled from lateral to medial across the arch followed by the second strip which will be pulled across the back of the heel and along the medial foot to the area of the first metatarsal head to secure the arch strap. The first portion 12 and the elongated strip 14 may be a unitary structure.

In use, the arch strap 10 provides a method for treating heel pain which comprises securing a first portion 12 shaped and sized to fit under the arch beneath a patient's foot along the lateral portion of the foot from the fifth metatarsal head to the back of the heel and extending upwardly along one side of the patient's foot to the medial portion of the foot and applying tension to an elongated strip having a first end attached to one side of the first portion 12 and extending around the patient's heel to a second end positioned at the other side of the foot. The elongated strip 14 will be pulled across the back of the heel 13 and along the medial foot to the area of the first metatarsal head to secure the arch strap 10, as shown in FIG. 2; thereby reducing tenderness, swelling and pain.

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An arch strap for the treatment of pain in the heel of a wearer's foot due to plantar fasciitis, posterior tibial tendonitis and capsulitis consisting essentially of:
    a first portion shaped and sized to fit only under the arch beneath a wearer's foot, along the lateral portion of said wearer's foot from the fifth metatarsal head to the heel said first portion extending upwardly along each side of said wearer's foot;
    an elongated elastic strip having a first end attached to one side of said first portion and configured to extend around the back of the wearer's heel to a second end of said elongated elastic strip configured to be positioned at the other side of said wearer's foot where said second end is attached to said other side of said first portion;
    said first portion being configured to be held in place on said wearer's arch by an adhesive.
2. The arch strap according to claim 1 wherein said arch strap is a unitary structure.
3. The arch strap according to claim 1 wherein said first portion serves as a pad.
4. The arch strap according to claim 1 wherein said elongated elastic strip has an adhesive portion.

* * * * *